United States Patent
Kazuno et al.

(10) Patent No.: US 8,838,411 B2
(45) Date of Patent: Sep. 16, 2014

(54) BED DEVICE

(75) Inventors: Hiroki Kazuno, Tokyo (JP); Jun Kawaguchi, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 408 days.

(21) Appl. No.: 13/376,370

(22) PCT Filed: May 7, 2010

(86) PCT No.: PCT/JP2010/057825
§ 371 (c)(1),
(2), (4) Date: Dec. 5, 2011

(87) PCT Pub. No.: WO2010/143487
PCT Pub. Date: Dec. 16, 2010

(65) Prior Publication Data
US 2012/0078573 A1 Mar. 29, 2012

(30) Foreign Application Priority Data
Jun. 11, 2009 (JP) ................................. 2009-140230

(51) Int. Cl.
G06F 15/00 (2006.01)
G01G 19/52 (2006.01)
G01G 19/44 (2006.01)
G01G 19/50 (2006.01)
A61B 5/00 (2006.01)
A61G 7/05 (2006.01)
A61B 5/11 (2006.01)

(52) U.S. Cl.
CPC ............ *G01G 19/50* (2013.01); *A61 2203/44* (2013.01); *G01G 19/445* (2013.01); *A61G 2203/32* (2013.01); *A61B 5/6892* (2013.01); *A61G 2007/0527* (2013.01); *A61B 5/1118* (2013.01)
USPC ............. 702/173; 600/527; 600/595; 600/587

(58) Field of Classification Search
CPC ............... A61B 5/6892; A61B 5/1118; A61B 2203/44; A61B 2007/10527; A61B 2203/32; G01G 19/445; G01G 19/50; G01G 5/11; G01G 5/4806

USPC ........ 702/173; 600/527, 595, 587; 340/573.3, 340/666
See application file for complete search history.

(56) References Cited

U.S. PATENT DOCUMENTS 3,890,958 A * 6/1975 Fister et al. .................... 600/527
5,008,654 A * 4/1991 Callaway ................... 340/573.1

(Continued)

FOREIGN PATENT DOCUMENTS

| CN | 101095612 A | 1/2008 |
| CN | 101313877 A | 12/2008 |

(Continued)

OTHER PUBLICATIONS

Roger J. Cole, et al.,"Automatic Sleep/Wake Identification From is Activity," Sleep, 15(5), pp. 461-469 (1992).

(Continued)

*Primary Examiner* — Carol S. W. Tsai
(74) *Attorney, Agent, or Firm* — McGinn IP Law Group, PLLC (57) ABSTRACT

A bed device has a load measurement unit for generating a load signal; a first computation unit for computing a center-of-gravity variation or load variation on the basis of the load signal; a first determination unit for determining whether the computation result for the center-of-gravity variation or load variation is equal to or greater than a first threshold value; a totaling unit for totaling the number of times that the computation result is determined to be equal to or greater than the first threshold value; a second computation unit for multiplying the totaling results by coefficients for each time period and adding the results; and a second determination unit or determining a waking or sleeping state or determining a body movement or rest state of a user on the basis of whether a computation result of the second computation unit is equal to or greater than a second threshold value.

15 Claims, 6 Drawing Sheets

(56) References Cited

U.S. PATENT DOCUMENTS

| | | | |
|---|---|---|---|
| 5,276,432 A | 1/1994 | Travis | |
| 6,036,660 A * | 3/2000 | Toms | 600/595 |
| 6,133,837 A * | 10/2000 | Riley | 340/573.1 |
| 6,646,556 B1 * | 11/2003 | Smith et al. | 340/573.1 |
| 7,253,366 B2 * | 8/2007 | Bhai | 177/45 |
| 7,437,787 B2 * | 10/2008 | Bhai | 5/613 |
| 7,664,606 B2 | 2/2010 | Suzuki et al. | |
| 2002/0070867 A1 * | 6/2002 | Conway et al. | 340/573.1 |
| 2004/0046668 A1 * | 3/2004 | Smith et al. | 340/573.7 |
| 2006/0038350 A1 * | 2/2006 | Weber | 273/371 |
| 2007/0118054 A1 * | 5/2007 | Pinhas et al. | 600/587 |
| 2007/0191742 A1 * | 8/2007 | Park | 600/587 |
| 2008/0004811 A1 | 1/2008 | Suzuki et al. | |
| 2009/0260158 A1 | 10/2009 | Kazuno et al. | |
| 2013/0245502 A1 * | 9/2013 | Lange et al. | 600/595 |

FOREIGN PATENT DOCUMENTS

| | | |
|---|---|---|
| JP | 02-280733 A | 11/1990 |
| JP | 3093745 B2 | 7/2000 |
| JP | 3322632 B2 | 6/2002 |
| JP | 3536043 B2 | 3/2004 |
| JP | 2007-190269 A | 8/2007 |
| JP | 2008-006005 A | 1/2008 |
| JP | 2008-212306 A | 9/2008 |
| JP | 2009-039453 A | 2/2009 |
| JP | 2009-118980 A | 6/2009 |
| WO | WO 2005/107674 A2 | 11/2005 |

OTHER PUBLICATIONS

J.C. Barbenel, et at, "Monitoring the mobility of patients in bed," Medical & Biological Engineering Computing, pp. 466-468 (Sep. 1985).

Chinese Office Action dated Sep. 27, 2012, with English translation.

English translation of Comments for Notification of First Office Action issued on Sep. 27, 2012.

European Search Report dated Feb. 11, 2014.

* cited by examiner

BED DEVICE

TECHNICAL FIELD

The present invention relates to a bed device whereby the wakefulness or body movement state of a bed user can be detected with high precision, for patients with delirium, new postoperative patients, and other patients.

BACKGROUND ART

Wandering by elderly with dementia, and stumbling/falling accidents around beds have recently become societal problems, and there is a need to address these problems. By using bed load information to monitor the in-bed movement of elderly and new postoperative patients and other users who are in bed for long periods of time, it may be possible to more rapidly respond when abnormal circumstances occur.

As an example of a technique for using bed load information to determine the state of a user, Patent Citation 1 discloses a technique for determining the in-bed or out-of-bed state of a user through use of bed load information. However, the technique disclosed in Patent Citation 1 is not designed to monitor the movement on the bed of a user who is continuously in bed for a long period of time.

As an example of a technique for monitoring the movement of a user on a bed, Non-patent Citation 1 discloses a technique in which a small acceleration sensor is mounted to the wrist of the user to measure movement of the user at each specific period of time, and the sleeping or waking state of the user is determined. However, this technique requires that a sensor be mounted to the body of the bed user, and is therefore unsuitable as a technique for elderly patients with dementia, new postoperative patients, and the like.

In order to overcome the problems of the conventional techniques described above, Patent Citations 2 through 5 and Non-patent Citation 2 disclose a technique for calculating a center of gravity from load information of four points on a bed and using the center-of-gravity information to monitor the movement of a user in the bed.

PRIOR ART CITATIONS

Patent Citations

[Patent Citation 1] Japanese Laid-open Patent Publication No. 2-280733
[Patent Citation 2] Japanese Patent No. 3093745
[Patent Citation 3] Japanese Patent No. 3322632
[Patent Citation 4] U.S. Pat. No. 5,276,432
[Patent Citation 5] Japanese Patent No. 3536043
[Patent Citation 6] Japanese Laid-open Patent Publication No. 2007-190269
[Patent Citation 7] Japanese Laid-open Patent Publication No. 2008-212306
[Patent Citation 8] Japanese Laid-open Patent Publication No. 2009-39453

Non-Patent Citations

[Non-patent Citation 1] Roger J. Cole et al., "Automatic Sleep/Wake Identification From Wrist Activity," *Sleep*, 15(5), pp. 461-469 (1992).
[Non-patent Citation 2] J. C. Barbenel et al., "Monitoring the mobility of patients in bed," *Medical & Biological Engineering & Computing*, pp. 466-468 (September 1985).

DISCLOSURE OF THE INVENTION

Problems that the Invention is Intended to Solve

However, in the conventional techniques described in Patent Citations 2 through 4, the amount of time for determining the amount of movement of the center of gravity must be increased in order to detect a slow arising with high precision. In this case it is impossible to detect a situation in which the user lies down after performing a lying down action/arising action in a shorter period than the time during which the user was previously up from bed for a long time.

In the techniques described in Patent Citations 2 through 5 and Non-patent Citation 2, by monitoring using only information that relates to the center of gravity of the user on the bed, even when it is possible to detect that the user is at an end of the bed, for example, it is impossible to distinguish whether the center of gravity has moved because the user is at the end part of the bed due to turning over while sleeping, the user is at the end part of the bed in order to get out of bed, or an object has been placed on the bed on which the user is sleeping or a person other than the user is leaning or sitting on the bed. The techniques described above also have drawbacks in that a movement of the center of gravity due to an action such as removing a railing or other accessory item is indistinguishable from an arising action, and determination errors sometimes occur.

Furthermore, in the technique disclosed in Patent Citation 5, the variation of the center of gravity is integrated, and the sleeping or waking state of the bed user is determined according to the integrated value. Consequently, when the bed user is sleeping, even in a case in which the variation of the center of gravity increases at only a single time due to a person other than the user leaning on or otherwise moving the bed, this large variation of the center of gravity due to a disturbance factor is used to determine the wakefulness of the bed user, and there is increased risk of a false positive indicating that the user is awake.

In order to overcome the problem of false positives described above, the present inventors have proposed bed devices in Patent Citations 6 through 8 in which false positives are minimized, and the movement of a user can be monitored with high detection precision by determining information in which user body weight information and center-of-gravity information are combined.

However, the techniques proposed in Patent Citations 6 through 8 are designed to detect an upright sitting state of the user, a sleep position, and arising, and not to detect the waking state or body movement state of the user. Consequently, in a case in which a patient receiving intravenous drip treatment in an intensive care unit or the like is monitored in a remote location from the bed, using the bed devices proposed in Patent Citations 6 through 8 does not enable the waking state or body movement state of the patient to be detected. Consequently, it is impossible to detect a situation in which a patient has removed his own drip line due to restless behavior.

The present invention was developed in view of the foregoing problems, and an object of the present invention is to provide a bed device whereby movement of a user can be monitored by using load information of a bed unit, and the waking state or body movement state of the bed user can be detected with high precision.

Means for Solving the Problems

The bed device according to the present invention comprises load measurement means for detecting a load of a bed unit and generating a load signal; first computation means for computing a center-of-gravity variation of the bed unit on the basis of the load signal; first determination means for determining whether the center-of-gravity variation computed by the first computation means is equal to or greater than a first threshold value; totaling means for totaling, over the course of a plurality of time periods backward from a specific time, the number of times that the center-of-gravity variation computed by the first computation means is determined to be equal to or greater than the first threshold value in each of fixed time periods; second computation means for multiplying the totaling results of the totaling means by coefficients established for each of the time periods and adding the results; and second determination means for determining a waking or sleeping state or determining a body movement or rest state of a user on the bed unit, on the basis of whether a computation result of the second computation means is equal to or greater than a second threshold value.

The bed device according to another aspect of the present invention comprises load measurement means for detecting a load of a bed unit and generating a load signal; first computation means for computing a load variation of the bed unit on the basis of the load signal; first determination means for determining whether the load variation computed by the first computation means is equal to or greater than a first threshold value; totaling means for totaling, over the course of a plurality of time periods backward from a specific time, the number of times that the load variation computed by the first computation means is determined to be equal to or greater than the first threshold value in each of fixed time periods; second computation means for multiplying the totaling results of the totaling means by coefficients established for each of the time periods and adding the results; and second determination means for determining a waking or sleeping state or determining a body movement or rest state of a user on the bed unit, on the basis of whether a computation result of the second computation means is equal to or greater than a second threshold value.

In the bed device described above, in a case in which the coefficients differ for each time period backward from the specific time, the second computation means applies a weighting to each of the totaling results by multiplying the totaling results by the coefficients, and the second determination means determines a waking or sleeping state of the user.

In a case in which the coefficients are equal for each of the time periods, the second determination means determines a body movement or rest state of the user.

A configuration may be adopted in which the bed device described above further comprises third computation means for computing the body weight of a user on the bed unit on the basis of the load signal; and third determination means for setting a third threshold value on the basis of the body weight of the user and determining that the user is out of bed in the case that the load of the bed unit is equal to or less than the third threshold value; wherein the computation results of the first and second computation means are deleted, and no determination is made by the first and second determination means in a time period in which the user is determined to be out of bed.

The bed device further comprises display means for displaying the determination result of the second determination means as the state of the user, for example.

Effect of the Invention

The bed device of the present invention is provided with a first determination means for determining whether the center-of-gravity variation on the bed unit is equal to or greater than a first threshold value. The totaling means then totals the number of center-of-gravity variations greater than or equal to the first threshold value for each fixed time period. In other words, the bed device of the present invention determines the state of the user on the basis of the number of times that a computed value is equal to or greater than a predetermined threshold value, rather than using the load signal as such to determine the waking or sleeping state or determine the body movement or rest state of the user on the bed unit. Consequently, even in cases in which a load due to a disturbance factor has a large temporary effect on the bed unit, the effect of the disturbance factor on the determination result is minimized, and the risk of false positive can be reduced.

The second computation means multiplies the totaling results by coefficients established for each time period and adds the results, and based on whether the computation result is equal to or greater than a second threshold value, the waking or sleeping state or the body movement or rest state of the user on the bed unit is determined. Consequently, the state of the user is monitored after the load signal has passed through four filters which include a filter by the first threshold value, a filter by the totaling means for totaling the number of times for each fixed time period, a filter by the second computation means, and a filter by the second threshold value. Consequently, it is possible to precisely monitor the state of the user over time while significantly reducing the risk of false positive due to disturbance factors.

In the bed device according to another aspect of the present invention, the first computation means computes the load variation on the bed unit. The first determination means then determines whether the load variation is equal to or greater than another first threshold value, and the totaling means totals the number of load variations that are greater than or equal to the other first threshold value for each fixed time period. In other words, the bed device according to another aspect of the present invention also does not use the load signal as such to determine the waking or sleeping state or determine the body movement or rest state of the user on the bed unit, and even in cases in which a load due to a disturbance factor has a large temporary effect on the bed unit, the effect of the disturbance factor on the determination result is minimized, and the risk of false positive can be reduced.

EMBODIMENTS FOR CARRYING OUT THE INVENTION

Figure 1:
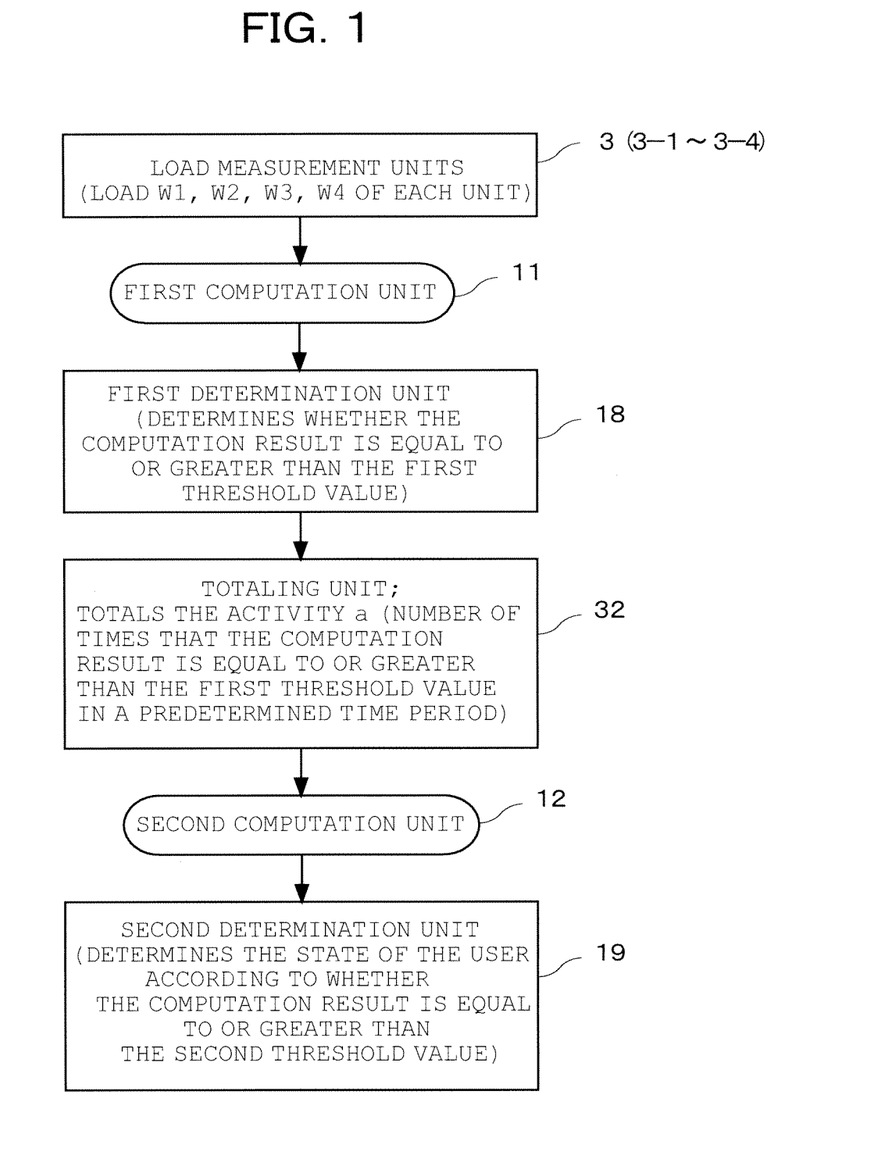
FIG. 1 is a block diagram showing the configuration of the bed device of the present invention.
Figure 2:
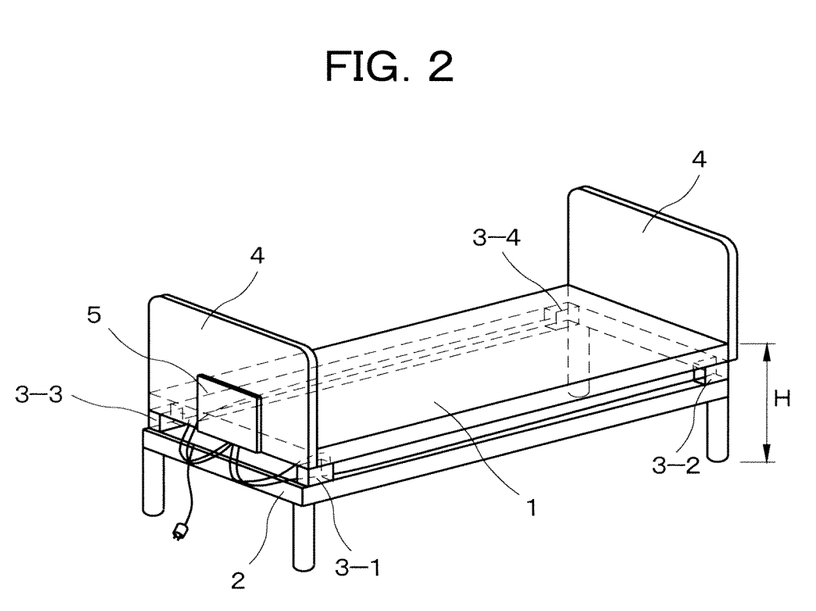
FIG. 2 is a schematic view showing the bed device according to a first embodiment of the present invention.
Figure 3:
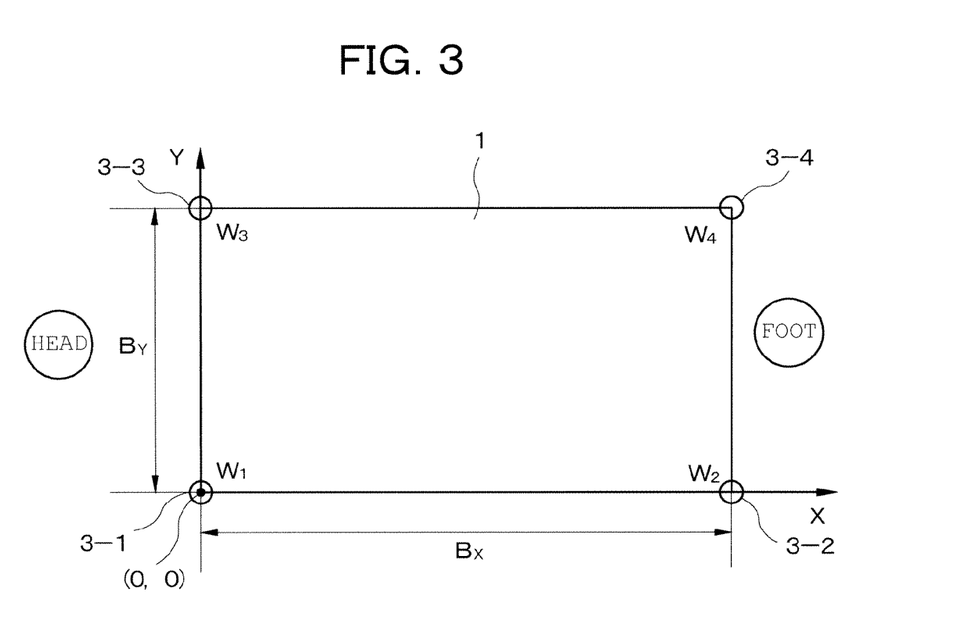
FIG. 3 is a schematic view showing an example in which four load sensors 3-1 through 3-4 are placed at the four ends of a bed unit 1.
Figure 4:
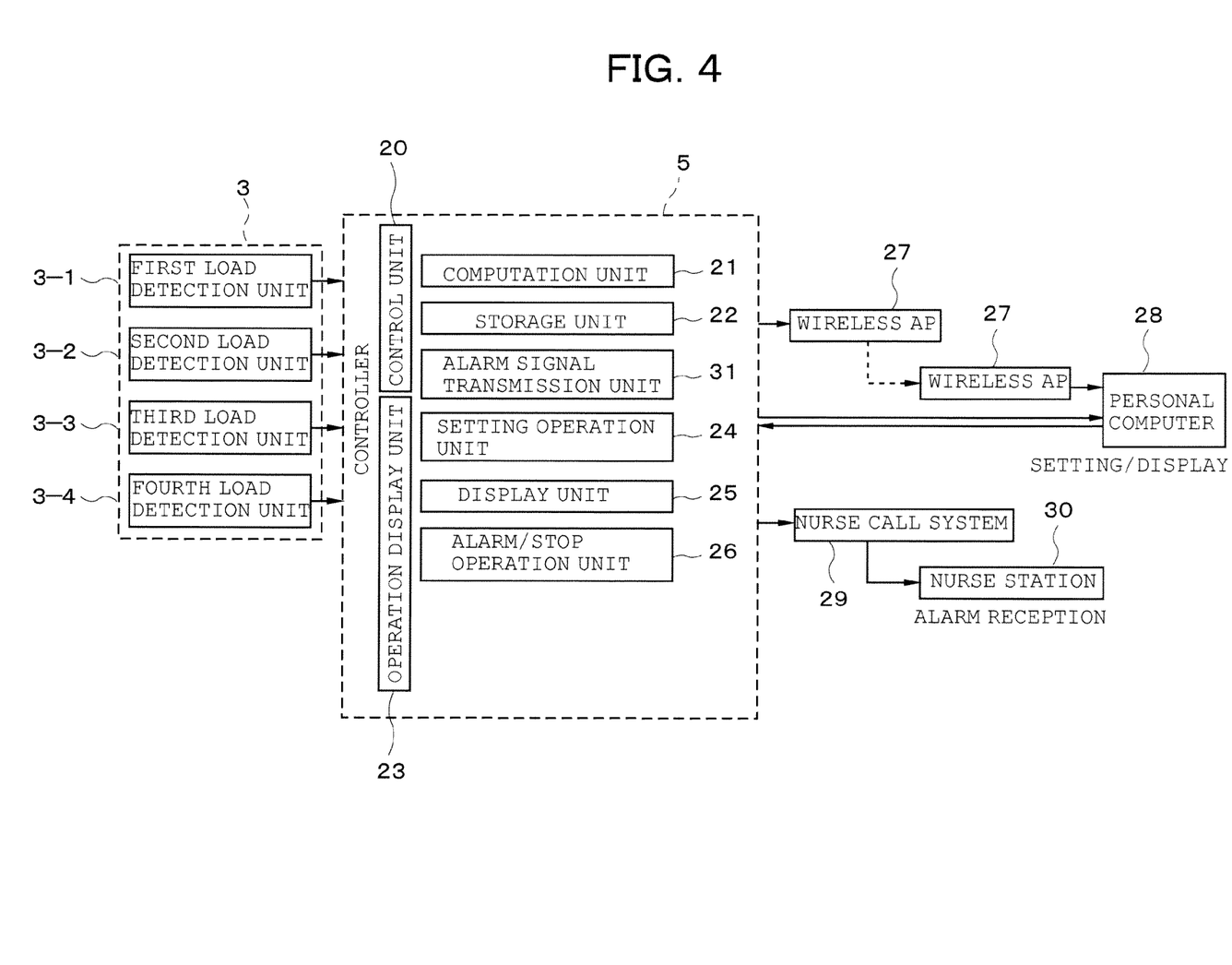
FIG. 4 is a block diagram showing the configuration of information processing of the signals of the load sensors 3 by a controller 5 and the execution of each function.
Figure 5:
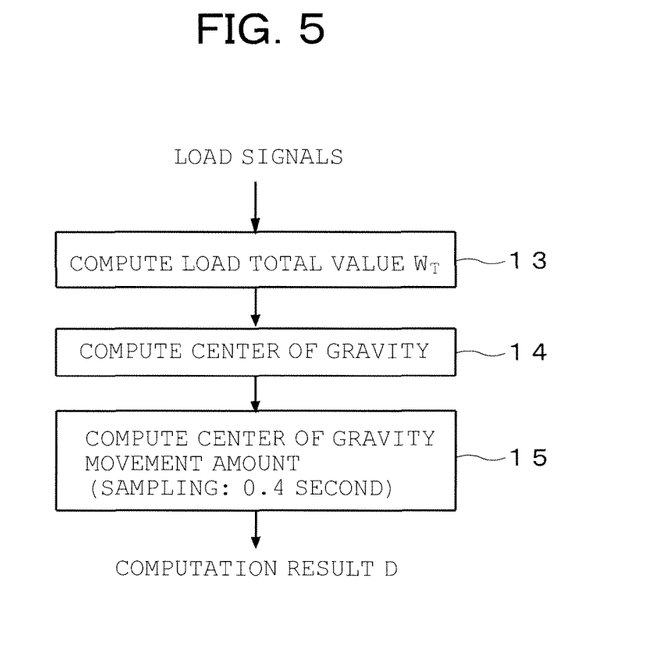
FIG. 5 is a block diagram showing the flow of computational processing by the first computation unit according to the first and second embodiments of the present invention.

Embodiments of the bed device of the present invention will be specifically described with reference to the accompanying drawings. FIG. 1 is a block diagram showing the configuration of the bed device of the present invention; FIG. 2 is a schematic view showing the bed device according to a first embodiment of the present invention; FIG. 3 is a schematic view showing an example in which four load sensors 3-1 through 3-4 are placed at the four ends of a bed unit 1; FIG. 4 is a block diagram showing the configuration of information processing of the signals of the load sensors 3 by a controller 5 and the execution of each function; and FIG. 5 is a block diagram showing the flow of computational processing by a first computation unit.

As shown in FIG. 1 the bed device of the present invention is provided with load measurement units 3 (3-1 through 3-4), a first computation unit 11, a first determination unit 18, a totaling unit 32, a second computation unit 12, and a second determination unit 19.

The load measurement units 3 (3-1 through 3-4) are provided at each of four corners of a frame 2 provided with legs for supporting a bed unit 1 shown in FIG. 2, and the load measurement units 3 are load sensors 3 (3-1, 3-2, 3-3, 3-4) for detecting a load on the bed unit 1 and generating load signals. The load signals generated by the load measurement units 3 are read at each fixed time by a controller 5 provided to one of two wall parts 4 provided at the narrow sides of the bed unit 1.

As shown in FIG. 4, the controller 5 is provided with a control unit 20 and a computation unit 21 which are configured so that processing in each of the first computation unit 11 depicted in FIG. 1, the second computation unit 12, the first determination unit 18, the second determination unit 19, and the totaling unit 32 is performed by software. The controller 5 is also provided with an alarm signal transmission unit 31 for generating an alarm signal; and a setting operation unit 24 for inputting first and second threshold values and various other setting values used in the respective determinations of the first and second determination units 18, 19. The controller 5 is also provided with a storage unit 22 for storing each setting value; a display unit 25 for displaying the state of the user on the basis of the determination results; and a nurse call system 29 or other alarm/stop operation unit 26. In each alarm device, an alarm signal is transmitted from the controller 5 to issue notification to a nurse station 30 via the nurse call system 29, or, in a case in which a plurality of beds is managed, an alarm signal is relayed through a LAN (Local Area Network) access point 27 from a communication connector to issue notification to a remote personal computer 28. At each of fixed times, the controller 5 reads the load signals generated by the load measurement units 3.

In the present embodiment, the first computation unit 11 is composed of a load total value computation unit 13, a center-of-gravity computation unit 14, and a center-of-gravity movement amount computation unit 15, as shown in FIG. 5. The load total value computation unit 13 computes an increment $W_T$ from a standard for the load total value on the bed unit 1, on the basis of the load signals generated by the load measurement units 3 read at each fixed time by the controller 5. Here, the standard for the load total value indicates the load total value in a state in which a mattress, bedding, and the like are mounted when there is no user on the bed unit 1. The center-of-gravity computation unit 14 computes the center of gravity based on the load total value $W_T$ computed by the load total value computation unit 13. As shown in FIG. 3, the side connecting the first load sensor 3-1 and the third load sensor 3-3 is the head side, and the side connecting the second load sensor 3-2 and the fourth load sensor 3-4 is the foot side. The left end of the head side of the bed unit 1 (lower left end of the bed unit 1 in FIG. 3) is designated as the origin (0, 0), the distance between the first load sensor 3-1 and the second load sensor 3-2 is designated as $B_X$, and the distance between the first load sensor 3-1 and the third load sensor 3-3 is designated as $B_Y$. The load total amount $W_T$ on the bed unit 1 is the sum of $W_1$ through $W_4$ ($W_1+W_2+W_3+W_4=W_T$), where $W_1$ through $W_4$ are the computed values of the load increment from the standard for the load signals generated by the first through fourth load sensors 3-1 through 3-4 when the user lies down on the bed unit 1 or when a load is placed on the bed unit 1 by placement of an object thereon. The center of gravity (X, Y) on the bed unit 1 can be expressed by Equation 1 below. The center-of-gravity computation unit 14 computes the center of gravity on the bed unit 1 according to this equation.

$$(X, Y) = \left( \frac{(W_2 + W_4) \cdot B_X}{W_T}, \frac{(W_3 + W_4) \cdot B_Y}{W_T} \right) \quad [\text{Eq. 1}]$$

The center-of-gravity movement amount computation unit 15 calculates the amount of movement of the center of gravity as described below. First, each time the computation unit 21 of the controller 5 reads the load signals for each fixed time, the center-of-gravity movement amount computation unit 15 computes the amount of movement of the center of gravity from the computation result for the current center of gravity by the load total value computation unit 13 and the center-of-gravity computation unit 14, and the computation result for a past center of gravity which is a center-of-gravity movement amount time difference $T_2$ in the past.

The movement amount $\Delta X$ of the center of gravity in the X-axis direction can be expressed by Equation 2 below, where $(X_2, Y_2)$ is the center of gravity of the user at a time $t_2$, and $(X_{2-T2}, Y_{2-T2})$ is the center of gravity in the past $t_{2-T2}$, which is a center-of-gravity movement amount time difference $T_2$ in the past from time $t_2$. The center-of-gravity movement amount computation unit 15 computes the movement amount $\Delta X$ of the center of gravity of the load on the bed unit 1 in the X-axis direction according to this equation. The movement amount $\Delta Y$ of the center of gravity of the load on the bed unit 1 in the Y-axis direction by substituting X with Y in Equation 2 below. The sampling time $T_2$ at this time is 0.4 seconds, for example.

$$\Delta X = X_2 - X_{2-T2} \text{(Amount of movement of the center of gravity in time difference } T_2\text{)} \quad [\text{Eq. 2}]$$

The center-of-gravity movement amount computation unit 15 then computes the center-of-gravity movement amount D according to Equation 3 below, based on the movement amounts $\Delta X$ and $\Delta Y$ of the center of gravity of the load on the bed unit 1 in the X-axis direction and the Y-axis direction. The computation result for the center-of-gravity movement amount D is then transmitted to the first determination unit 18 of the controller 5.

$$D = \sqrt{\Delta X^2 + \Delta Y^2} \quad [\text{Eq. 3}]$$

The first determination unit 18 provided to the controller 5 determines whether the center-of-gravity movement amount D is equal to or greater than a first threshold value. In the case that the first determination unit 18 determines that the center-of-gravity movement amount D is equal to or greater than the first threshold value, the determination result is transmitted to the totaling unit 32. For example, in a case in which the first threshold value is set to 1 cm, and the center of gravity moves five times with movement amounts of 5 cm, 1 cm, 1 cm, 0.5 cm, and 1 cm in a fixed time period (e.g., one minute) backward from a certain time $t_2$, the first determination unit 18 transmits a determination result to the totaling unit 32 each time a movement of the center of gravity occurs that is equal to or greater than the first threshold value. In other words, in the case of this example, movements of the center of gravity equal to or greater than the first threshold value occur four times, and the first determination unit 18 transmits a determination result to the totaling unit 32 four times.

The totaling unit 32 totals the determination results transmitted from the first determination unit 18 for each fixed time period (one minute in the example described above). In the case of the example described above, the totaling unit 32 derives the number four as the number of center-of-gravity movements that are equal to or greater than the first threshold value. The totaling unit 32 then totals, for each fixed time period, the number of center-of-gravity movements that are equal to or greater than the first threshold value, and transmits the totaling result to the second computation unit 12. When the fixed time period is one minute, and a center-of-gravity movement equal to or greater than the first threshold value occurs two times, one time, one time, three times, and zero times in five minutes, respectively, backward from a certain time $t_2$, for example, the totaling unit 32 transmits the numbers 2, 1, 1, 3, and 0 to the second computation unit 12 for each respective minute.

The second computation unit 12 then performs a predetermined computation on the basis of the totaling result transmitted from the totaling unit 32. In the present first embodiment, the second computation unit 12 adds the totaling result from the totaling unit 32 four time periods backward from a certain time in accordance with Equation 4 below. Here, J in Equation 4 is the computation result of the second computation unit 12. Also, a(0) is the number of times that the center-of-gravity movement amount D is determined to be equal to or greater than the first threshold value in the period from a time a certain time period in the past from time $t_2$, a certain time $t_2$ being a reference time, until a fixed time period elapses (until time $t_2$). In the same manner, a(−1) through a(−3) are the number of times that the center-of-gravity movement amount D is determined to be equal to or greater than the first threshold value in the period from the times two through four fixed time periods backward from time $t_2$, respectively, until the fixed time periods elapse. The second computation unit 12 then transmits the computation result J to the second determination unit 19.

$$J=a(0)+a(-1)+a(-2)+a(-3) \quad [\text{Eq. 4}]$$

The second determination unit 19 determines the state of the user on the bed unit 1 on the basis of whether the computation result of the second computation unit 12 is equal to or greater than a second threshold value. In the present embodiment, the second computation unit 12 adds a plurality of totaling results from the totaling unit 32, and the second determination unit 19 determines by this computation value whether the user on the bed unit 1 is moving or stationary. In other words, by adding the number of center-of-gravity movements that are equal to or greater than the first threshold over the course of a plurality of fixed time periods backward from time $t_2$ as the activity of the user, the number of relatively significant movements of the user on the bed unit 1 in a fixed time period is totaled, and the body movement or rest state of the user over time is determined. In the present embodiment, the second computation unit 12 simply adds up the number of center-of-gravity movements that are equal to or greater than the first threshold value, as shown in Equation 4, but the totaled values a(0) through a(−3) to be added may also be multiplied each by equal coefficients before being added together. In this case, the second threshold value is also set to an appropriate size in accordance with the coefficient by which each totaled value is multiplied in common.

The second determination unit 19 transmits the determination result for the body movement or rest state of the user to the display unit 25 and the alarm signal transmission unit 31. The display unit 25 displays the determined state of the user on a monitor. In each alarm device, an alarm signal is transmitted from the controller 5 to issue notification to a nurse station 30 via the nurse call system 29, or, in a case in which a plurality of beds is managed, an alarm signal is relayed through a LAN (Local Area Network) access point 27 from a communication connector to issue notification to a remote personal computer 28. The state of the user can thereby be managed at a remote location.

The invention according to the present first embodiment is configured as described below. Specifically, the bed device of the invention according to the first embodiment is characterized in comprising load measurement means for detecting a load of a bed unit and generating a load signal; first computation means for computing a load variation of the bed unit on the basis of the load signal; first determination means for determining whether the load variation computed by the first computation means is equal to or greater than a first threshold value; totaling means for totaling, over the course of a plurality of time periods backward from a specific time, the number of times that the load variation computed by the first computation means is determined to be equal to or greater than the first threshold value in each of fixed time periods; second computation means for adding a plurality of totaling results of the totaling means; and second determination means for determining a body movement or rest state of a user on the bed unit, on the basis of whether a computation result of the second computation means is equal to or greater than a second threshold value.

In the invention according to the present first embodiment, when a center-of-gravity variation occurs that is equal to or greater than the first threshold value, the number of changes in the center of gravity is totaled for each fixed time period, and the plurality of results is added together. The user on the bed unit is then determined to be in a state of body movement or rest according to whether the value totaled by the totaling means is equal to or greater than the second threshold value. In the case that the object is to monitor the movement of delirious patients, new postoperative patients, and the like, such as in the present invention, it is necessary to detect with high precision whether a patient is in a state of body movement or rest. In the present first embodiment, the number of times that the center-of-gravity movement amount D is determined to be equal to or greater than the first threshold value within a fixed time period is totaled by the totaling unit 32 as the activity of the user on the bed unit 1. When the bed user is sleeping on the bed unit 1, even in a case in which there is a large center-of-gravity variation at only a single time due to a disturbance factor such as a person other than the user leaning on the bed unit, a movement of the center of gravity equal to or greater than the first threshold value occurs only once. Consequently, compared with the conventional technique in which the sleeping or waking state of the bed user is determined by the value obtained by simply integrating the variations of the center of gravity, the activity of the user on the bed unit 1 can be precisely monitored, and the risk of false positive can be reduced.

In the example described above in which the center of gravity moves five times with a center-of-gravity movement amount D of 5 cm, 1 cm, 1 cm, 0.5 cm, and 1 cm in a time period a fixed time period backward from a certain time t2, a value of 8.5 cm obtained as a result of integrating 5 cm+1 cm+1 cm+0.5 cm+1 cm is used for the determination in the conventional technique. However, in the case that the center-of-gravity movement amount D due to the disturbance factor is 5 cm, the value that should be used in the actual determination is only 3.5 cm of the total 8.5 cm. In other words, in the conventional waking determination, even in the case that the user is asleep, the large center-of-gravity variation due to the disturbance factor is used to determine the waking state of the bed user, and there is a risk that the user will be falsely determined as being awake. In the present embodiment, however, the threshold value of the center-of-gravity movement amount D is set to 1 cm, and movements of the center of gravity less than this threshold value are not totaled as the activity of the user on the bed unit 1. Consequently, the risk of false positive can be reduced in cases in which movements of the center of gravity due to disturbance factors are minimal. Of the four movements totaled by the totaling unit 32 as the number of center-of-gravity movements that are equal to or greater than the first threshold value, one movement of the center of gravity is due to a disturbance factor. Thus, instead of using changes in the center of gravity simply as variations to determine body movement, the number of center-of-gravity movements is used to determine body movement of the user in the case that there is a movement of the center of gravity equal to or greater than a predetermined threshold value. The effect of disturbance factors on the determination result is thereby reduced, and the risk of false positive can be reduced.

In the present embodiment, the second computation unit 12 furthermore adds together the number of center-of-gravity movements that are equal to or greater than the first threshold value over the course of a plurality of fixed time periods backward from the reference time. Moreover, the body movement state of the user is determined according to whether the computed number of center-of-gravity movements is equal to or greater than the second threshold value. Consequently, even in cases in which there is a temporary significant movement of the center of gravity by a disturbance factor, the effect of the disturbance factor on the determination result is minimized, and the risk of false positive can be reduced. In other words, by the bed device of the present embodiment, the body movement of the user is monitored via four filters which include a filter by the first threshold value, a filter by totaling the number of center-of-gravity movements, a filter by adding the number of center-of-gravity movements equal to or greater than the threshold value in a plurality of fixed time periods, and a filter by the second threshold value. Consequently, it is possible to monitor the body movement state of the user over time in real time while significantly reducing the risk of false positive due to disturbance factors.

In the present embodiment, the number of center-of-gravity movements in a time period four fixed time periods backward from time $t_2$ is used to determine the body movement state of the user, but the number of time periods in the past may be increased as appropriate in such cases as when the set fixed time period is short. In this case, the number of computation values a(0) through a(−3) added in Equation 4 above may be increased. The number of time periods in the past may also be reduced as appropriate in such cases as when the set fixed time period is long. In this case as well, the number of computation values a(0) through a(−3) added in Equation 4 above may be reduced.

A second embodiment of the present invention will next be described. The bed device of the second embodiment is the same as that of the first embodiment in being provided with load sensors 3 (3-1, 3-2, 3-3, 3-4) as load measurement units, a first computation unit 11 for computing the center-of-gravity movement amount D from the load total value $W_T$ and the center of gravity ($X_2$, $Y_2$), a first determination unit 18 for determining whether the center-of-gravity movement amount D is equal to or greater than a first threshold value, a totaling unit 32 for totaling the number of times that the center-of-gravity movement amount D is equal to or greater than the first threshold value, and a second determination unit 19 for determining the state of the user on the basis of whether the computation result of the second computation unit 12 is equal to or greater than a second threshold value. However, the equation for computation in the second computation unit 12 is different in the second embodiment. In the present embodiment, the second determination unit 19 detects a waking or sleeping state of the user on the bed unit 1.

In the present second embodiment, the equation for computation in the second computation unit 12 is Equation 5 below. Specifically, the second computation unit 12 multiplies the totaling results transmitted from the totaling unit 32 by coefficients established for each fixed time period before adding the results. As in the first embodiment, J in Equation 5 is the computation result of the second computation unit 12. Also, a(0) is the number of times that the center-of-gravity movement amount D is determined to be equal to or greater than the first threshold value in the period from a time a certain time period in the past from time $t_2$, a certain time $t_2$ being a reference time, until a fixed time period elapses (until time $t_2$). In the same manner, a(−1) through a(−4) are the number of times that the center-of-gravity movement amount D is determined to be equal to or greater than the first threshold value in the period from the times two through five fixed time periods backward from time $t_2$, respectively, until a fixed time period elapses. The values w(0) through w(−4) are coefficients for each time period by which the totaling results of the totaling unit 32 are multiplied, and vary according to how far backward the time period of each totaling result is from time $t_2$. Specifically, the coefficient multiplied by the totaling result a(0) of the totaling unit is w(0) in the period from a time a fixed time period backward from time t2 until the fixed time period elapses (until time t2), and the coefficients multiplied by the totaling results a(−1) through a(−4) are w(−1) through w(−4), respectively, in the periods from times two through five fixed time periods backward from time t2 until the fixed time periods elapse. In the present second embodiment, different coefficients are thus established for each time period backward from a certain specific time, and the coefficients are multiplied by the totaling results as weighting coefficients for each time period.

$$J=w(0)\times a(0)+w(-1)\times a(-1)+w(-2)\times a(-2)+w(-3)\times a(-3)+w(-4)\times a(-4) \qquad [\text{Eq. 5}]$$

The second determination unit 19 determines the sleeping or waking state of the user on the bed unit 1 on the basis of whether the computation result of the second computation unit 12 is equal to or greater than a second threshold value. As shown in Equation 5 above, in the present second embodiment, the second computation unit 12 adds the plurality of computation results after multiplying the totaling results from the totaling unit 32 by predetermined coefficients as weighting coefficients which vary for each fixed time period. The second determination unit 19 then determines by this computation value whether the user on the bed unit 1 is in a waking state or a sleeping state. In other words, by multiplying coefficients established for each time period by the number of center-of-gravity movements equal to or greater than the first threshold value, and weighting the computation results for each fixed time period over the course of a plurality of fixed time periods backward from time $t_2$, the change in the movement of the user in time periods backward from a reference time can be monitored over time, and it is possible to monitor the waking state or sleeping state of the user over time.

The number of center-of-gravity movements in a time period five fixed time periods backward from time $t_2$ is used in the present embodiment as well to determine the waking state of the user, but the number of time periods in the past may be increased as appropriate in such cases as when the set fixed time period is short. In this case, the number of computation values $a(0)$ through $a(-4)$ added in Equation 5 above may be increased. The number of time periods in the past may also be reduced as appropriate in such cases as when the set fixed time period is long. In this case as well, the number of computation values $a(0)$ through $a(-4)$ added in Equation 5 above may be reduced.

Figure 6:
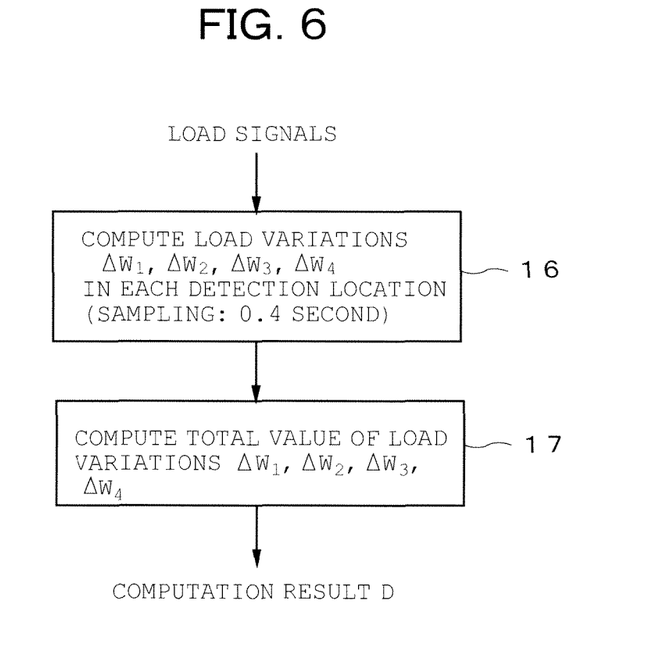
FIG. 6 is a block diagram showing the flow of computational processing by the first computation unit according to the third and fourth embodiments of the present invention.

A third embodiment of the present invention will next be described. In the third embodiment, the first computation unit 11 is composed of a load variation computation unit 16 and a load variation total value computation unit 17, as shown in FIG. 6. Other aspects of the configuration of the third embodiment are the same as in the first embodiment. The load variation computation unit 16 computes load increments $W_1$ through $W_4$ from standards for the load signals generated by the first through fourth load sensors 3-1 through 3-4, on the basis of the load signals generated by the load sensors 3 read by the controller 5 at each fixed time. The variations $\Delta W_1$ through $\Delta W_4$ of the loads in the sensors 3-1 through 3-4, respectively, are computed as absolute values from the loads at a certain time $t_2$ and past loads a certain time difference $T_2$ backward from time $t_2$. The sampling time $T_2$ at this time is 0.4 seconds, for example. The load variation total value computation unit 17 then adds together the load variations $\Delta W_1$ through $\Delta W_4$ computed by the load variation computation unit 16 to compute the total value of the load variation, and transmits the result as the computation result D to the first determination unit 18 of the controller 5.

The first determination unit 18 provided to the controller 5 then determines whether the computation result D of the first computation unit 11 is equal to or greater than the first threshold value, and in the case that the total load variation on the bed unit 1 is equal to or greater than the first threshold value, the determination result is transmitted to the totaling unit 32. In the present embodiment, the determination by the first determination unit 18 is performed based on the total value of the load variation. Consequently, the first threshold value set as a movement amount (length) in the first embodiment is a load (weight) in the present embodiment.

Totaling in the totaling unit 32 is performed for each fixed time period, the same as in the first and second embodiments. For example, in the case of detecting the activity of a user at a certain time $t_2$, the totaling unit 32 totals for each time period the number of times $a(-n)$ that the total value D of the load variation is equal to or greater than the first threshold value in the period from the time n+1 fixed time periods backward from time $t_2$ until the fixed time period elapses, such that $a(0)$ is the number of times that the total value D of the load variation is equal to or greater than the first threshold value in the period from the time a fixed time period (e.g., one minute) backward from time $t_2$ until time $t_2$, and $a(-1)$ is the number of times that the total value D of the load variation is equal to or greater than the first threshold value in the period from the time two fixed time periods backward from time $t_2$ until the fixed time period elapses. The method of computation in the second computation unit 12 and the method of determination in the second determination unit 19 thereafter are the same as in the first embodiment. The second determination unit 19 then determines whether the user is in a state of body movement or rest.

In the present third embodiment, determination is made based on the number of load variations equal to or greater than the first threshold value, rather than on center-of-gravity movements. In determining body movement of the user, rather than simply using the value D obtained by integrating the load variations $\Delta W_4$ through $\Delta W_4$ to determine body movement, a determination is first made as to whether the value D is equal to or greater than the first threshold value, and in the case that the computation result D is equal to or greater than the first threshold value, the number of times that the computation result D is equal to or greater than the first threshold value is totaled by the totaling unit 32. In other words, load variations of less than the threshold value are not totaled as the activity of the user on the bed unit 1. Consequently, the risk of false positive can be reduced in cases in which movements of the center of gravity due to disturbance factors are minimal. When the bed user is sleeping on the bed unit 1, even in a case in which the load variation increases at only a single time due to a disturbance factor such as a person other than the user leaning on the bed, the number of load variations equal to or greater than the first threshold value is one. Consequently, as in the first embodiment, the activity of the user on the bed unit 1 can be precisely monitored, and the risk of false positive can be reduced in comparison with the conventional technique in which the sleeping or waking state of the bed user is determined by the value obtained by simply integrating the variations.

In the present embodiment as well, the second computation unit 12 adds together the number of load variations that are equal to or greater than the first threshold value over the course of a plurality of fixed time periods backward from the reference time. Moreover, the body movement or rest state of the user is determined according to whether the computed number of load variations equal to or greater than the first threshold value is equal to or greater than the second threshold value. Consequently, even in cases in which there is a temporary significant movement of the center of gravity by a disturbance factor, the effect of the disturbance factor on the determination result is minimized, and the risk of false positive can be reduced. In other words, by the bed device of the present embodiment, the body movement of the user is monitored via four filters which include a filter by the first threshold value, a filter by totaling the number of load variations equal to or greater than the first threshold value, a filter by adding the number of load variations equal to or greater than the threshold value over the course of a plurality of fixed time periods, and a filter by the second threshold value. Consequently, it is possible to monitor the body movement state of the user over time in real time while significantly reducing the risk of false positive due to disturbance factors.

A fourth embodiment of the present invention will next be described. In the bed device of the fourth embodiment, computation in the second computation unit 12 is performed by Equation 5 above, the same as in the second embodiment. The second determination unit 19 detects the waking or sleeping state of the user on the bed unit 1. Specifically, the second computation unit 12 multiplies the totaling results from the totaling unit 32 by different coefficients established for each time period as weighting coefficients for each time period, and adds together the plurality of results. By this computation value, the second determination unit 19 then determines whether the user on the bed unit 1 is in a waking state or a sleeping state.

In the present embodiment as well, by multiplying the number of load variations equal to or greater than the first threshold value by different coefficients established for each time period in a plurality of fixed time periods backward from time t2, and weighting the computation results for each fixed time period, the change in the movement of the user in time periods backward from a reference time can be monitored over time, and it is possible to monitor the waking state or sleeping state of the user over time, the same as in the second embodiment.

Figure 7:
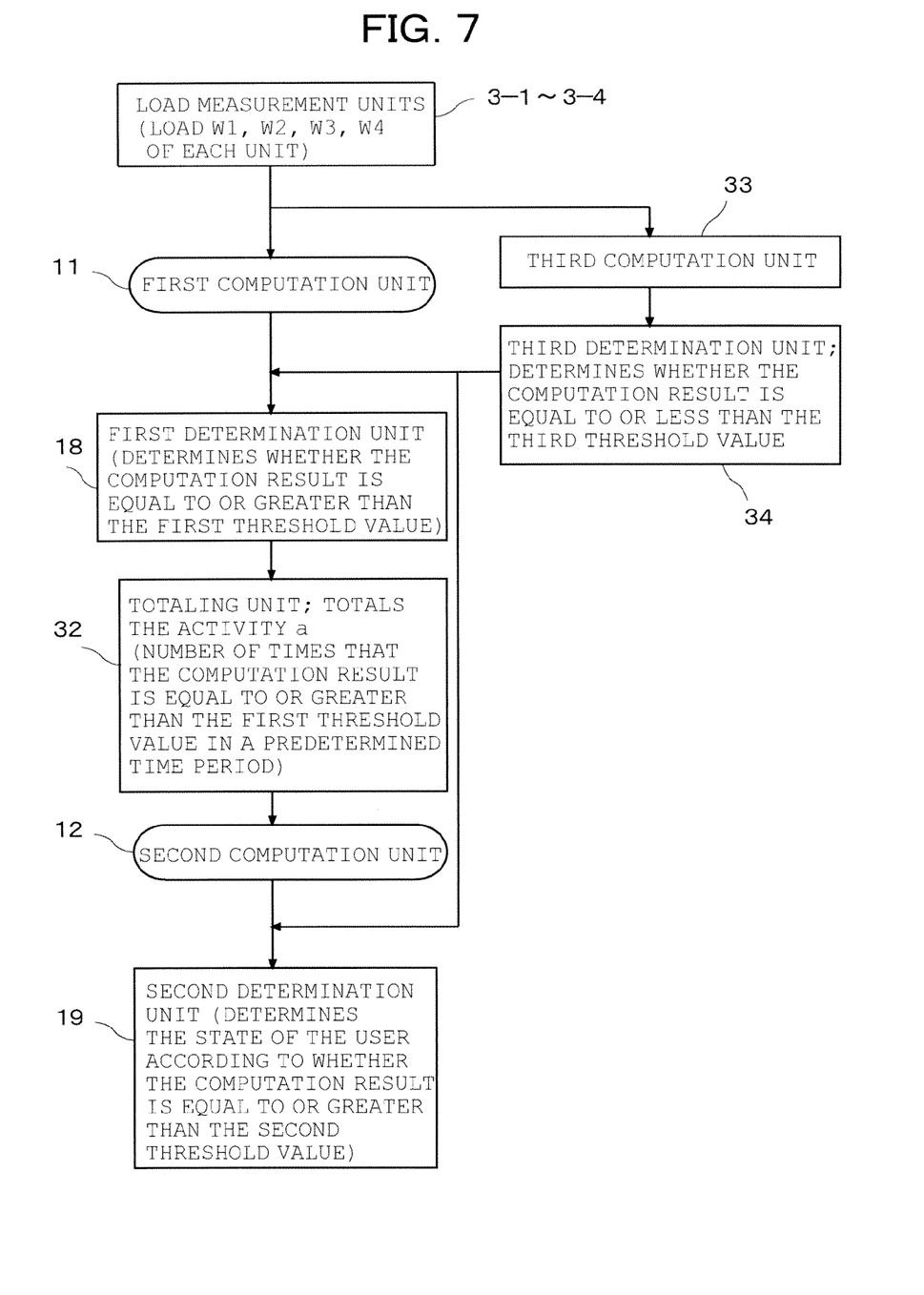
FIG. 7 is a block diagram showing the configuration of the bed device according to the fifth embodiment of the present invention.

A fifth embodiment of the present invention will next be described. As shown in FIG. 7, in the bed device of the present fifth embodiment, a third computation unit 33 for computing the body weight of a user on the bed unit 1, and a third determination unit 34 are further provided to the bed device of the first embodiment. The third computation unit 33 computes the body weight of the user on the bed unit on the basis of computed values $W_1$ through $W_4$ of the load increment from the standard for the load signals generated by the first through fourth load sensors 3-1 through 3-4 when the user lies down on the bed unit 1.

The third determination unit 34 then sets a third threshold value on the basis of the body weight of the user computed by the third computation unit 33. The third threshold value is a value obtained by multiplying the body weight of the user on the bed unit 1 by a predetermined coefficient (e.g., 1.2), for example. The third determination unit 34 then determines whether the load on the bed unit 1 is equal to or less than the third threshold value. In the time period in which the load on the bed unit 1 is determined to be equal to or less than the third threshold value, the third determination unit 34 transmits the determination result between the first computation unit 11 and the first determination unit 18 and between the second computation unit 12 and the second determination unit 19, and deletes the computation results of the first and second computation units 11, 12. In other words, the respective determinations of the first and second determination units 18, 19 are not made during the time period in which the load on the bed unit 1 is determined to be equal to or less than the third threshold value.

In the present embodiment, providing the third computation unit 33 and the third determination unit 34 makes it possible to detect whether the user is in bed or out of bed. In the case that the load on the bed unit 1 is equal to or less than the third threshold value, i.e., the user is out of bed, the respective determinations of the first and second determination units 18, 19 are not made. The computation results in the time period in which the user is determined to be out of bed are thus not used to determine the body movement or rest state of the user. The robustness of the determination results can thereby be enhanced, and the activity of the user can be more precisely monitored.

The third computation unit 33 and third determination unit 34 of the present embodiment may also be provided to the bed devices of the second through fourth embodiments. The robustness of the determination results can be enhanced in this case as well by not using the computation results for the time period in which the user is determined to be out of bed to determine the waking or sleeping state or determine the body movement or rest state of the user.

In the bed device of the present invention described above, by totaling the number of times that the total value of center-of-gravity variations or load variations is equal to or greater than the first threshold value, the risk of false positive can be reduced in comparison with the conventional technique in which a center-of-gravity variation or load variation is simply used to determine waking. In the embodiments described above, the total value of the center-of-gravity variation or the load variation is measured with a sampling period of 0.4 second. In this case, determining that the user on the bed unit is in a body movement or waking state when a center-of-gravity variation or load variation that exceeds the first threshold value occurs five or more times, for example, in one minute, for example, can be taken as being equivalent to a center-of-gravity variation or load variation that exceeds the first threshold value occurring for 2.0 seconds in one minute. In other words, the bed device of the present invention may be configured so as to total the time periods during which center-of-gravity variations or load variations occur that exceed the first threshold value. The same effects are obtained in this case as in the embodiments described above.

INDUSTRIAL APPLICABILITY

The present invention is capable of highly precise detection of the waking state or body movement state of a bed user, and is therefore extremely effective for preventing stumbling/falling accidents around beds by elderly or patients with dementia and the like.

KEY TO SYMBOLS

1: bed unit
2: frame
3: load sensors
3-1: first load sensor
3-2: second load sensor
3-3: third load sensor
3-4: fourth load sensor
4: wall parts
5: controller
11: first computation unit
12: second computation unit
13: body weight computation unit
14: center-of-gravity computation unit
15: center-of-gravity movement amount computation unit
16: load variation computation unit
17: load variation total value computation unit
18: first determination unit
19: second determination unit
20: control unit
21: computation unit
22: storage unit
23: operation display unit
24: setting operation unit
25: display unit
26: alarm/stop operation unit
27: LAN AP
28: personal computer
29: nurse call system
30: nurse station
31: alarm signal transmission unit
32: totaling unit
33: third computation unit
34: third determination unit

The invention claimed is:

1. A bed device comprising:
load measurement means for detecting a load of a bed unit and generating a load signal;
first computation means for computing a center-of-gravity variation of said bed unit on the basis of said load signal;

first determination means for determining whether the center-of-gravity variation computed by the first computation means is equal to or greater than a first threshold value;

totaling means for totaling, over the course of a plurality of time periods backward from a specific time, the number of times that the center-of-gravity variation computed by said first computation means is determined to be equal to or greater than said first threshold value in each of fixed time periods;

second computation means for multiplying the totaling results of said totaling means by coefficients established for each of said time periods and adding the results; and second determination means for determining a waking or sleeping state or determining a body movement or rest state of a user on said bed unit, on the basis of whether a computation result of the second computation means is equal to or greater than a second threshold value.

2. A bed device comprising:

load measurement means for detecting a load of a bed unit and generating a load signal;

first computation means for computing a load variation of said bed unit on the basis of said load signal;

first determination means for determining whether the load variation computed by the first computation means is equal to or greater than a first threshold value;

totaling means for totaling, over the course of a plurality of time periods backward from a specific time, the number of times that the load variation computed by said first computation means is determined to be equal to or greater than said first threshold value in each of fixed time periods;

second computation means for multiplying the totaling results of said totaling means by coefficients established for each of said time periods and adding the results; and second determination means for determining a waking or sleeping state or determining a body movement or rest state of a user on said bed unit, on the basis of whether a computation result of the second computation means is equal to or greater than a second threshold value.

3. The bed device according to claim 1, wherein
said coefficients differ for each time period backward from said specific time;
said second computation means applies a weighting to each of the totaling results by multiplying said totaling results by said coefficients; and
said second determination means determines a waking or sleeping state of said user.

4. The bed device according to claim 1, wherein
said coefficients are equal for each of said time periods; and
said second determination means determines a body movement or rest state of said user.

5. The bed device according to claim 1, further comprising:
third computation means for computing the body weight of a user on said bed unit on the basis of said load signal; and
third determination means for setting a third threshold value on the basis of the body weight of said user and determining that said user is out of bed in the case that the load of said bed unit is equal to or less than said third threshold value; wherein
the computation results of said first and second computation means are deleted, and no determination is made by said first and second determination means in a time period in which said user is determined to be out of bed.

6. The bed device according to claim 1, further comprising display means for displaying the determination result of said second determination means as the state of said user.

7. The bed device according to claim 2, wherein
said coefficients differ for each time period backward from said specific time;
said second computation means applies a weighting to each of the totaling results by multiplying said totaling results by said coefficients; and
said second determination means determines a waking or sleeping state of said user.

8. The bed device according to claim 2, wherein
said coefficients are equal for each of said time periods; and
said second determination means determines a body movement or rest state of said user.

9. The bed device according to claim 2, further comprising:
third computation means for computing the body weight of a user on said bed unit on the basis of said load signal; and
third determination means for setting a third threshold value on the basis of the body weight of said user and determining that said user is out of bed in the case that the load of said bed unit is equal to or less than said third threshold value; wherein
the computation results of said first and second computation means are deleted, and no determination is made by said first and second determination means in a time period in which said user is determined to be out of bed.

10. The bed device according to claim 3, further comprising:
third computation means for computing the body weight of a user on said bed unit on the basis of said load signal; and
third determination means for setting a third threshold value on the basis of the body weight of said user and determining that said user is out of bed in the case that the load of said bed unit is equal to or less than said third threshold value; wherein
the computation results of said first and second computation means are deleted, and no determination is made by said first and second determination means in a time period in which said user is determined to be out of bed.

11. The bed device according to claim 4, further comprising:
third computation means for computing the body weight of a user on said bed unit on the basis of said load signal; and
third determination means for setting a third threshold value on the basis of the body weight of said user and determining that said user is out of bed in the case that the load of said bed unit is equal to or less than said third threshold value; wherein
the computation results of said first and second computation means are deleted, and no determination is made by said first and second determination means in a time period in which said user is determined to be out of bed.

12. The bed device according to claim 2, further comprising display means for displaying the determination result of said second determination means as the state of said user.

13. The bed device according to claim 3, further comprising display means for displaying the determination result of said second determination means as the state of said user.

14. The bed device according to claim 4, further comprising display means for displaying the determination result of said second determination means as the state of said user.

15. The bed device according to claim 5, further comprising display means for displaying the determination result of said second determination means as the state of said user.

\* \* \* \* \*